United States Patent
Lu et al.

(10) Patent No.: US 12,344,622 B2
(45) Date of Patent: Jul. 1, 2025

(54) REFINING METHOD OF MIDBODY OF LATAMOXEF SODIUM

(71) Applicant: Hainan Hailing Chemipharma Corporation Ltd., Haikou (CN)

(72) Inventors: Yifeng Lu, Haikou (CN); Qin Cai, Haikou (CN); Xingyu Chen, Haikou (CN)

(73) Assignee: Hainan Hailing Chemipharma Corporation Ltd., Haikou (CN)

( * ) Notice: Subject to any disclaimer, the term of this patent is extended or adjusted under 35 U.S.C. 154(b) by 0 days.

(21) Appl. No.: 17/623,252

(22) PCT Filed: Dec. 15, 2021

(86) PCT No.: PCT/CN2021/138335
§ 371 (c)(1),
(2) Date: Dec. 28, 2021

(87) PCT Pub. No.: WO2023/284247
PCT Pub. Date: Jan. 19, 2023

(65) Prior Publication Data
US 2024/0043449 A1    Feb. 8, 2024

(30) Foreign Application Priority Data
Jul. 14, 2021 (CN) .......... 202110792892.3

(51) Int. Cl.
*C07D 505/06* (2006.01)
*C07D 505/16* (2006.01)

(52) U.S. Cl.
CPC ......... *C07D 505/06* (2013.01); *C07D 505/16* (2013.01)

(58) Field of Classification Search
CPC ... C07D 505/00; C07D 505/02; C07D 506/02
See application file for complete search history.

(56) References Cited

FOREIGN PATENT DOCUMENTS

| CN | 107586305 | * | 1/2018 |
| CN | 109485659 | * | 3/2019 |
| CN | 113387960 | * | 9/2021 |

\* cited by examiner

*Primary Examiner* — Susanna Moore
(74) *Attorney, Agent, or Firm* — JEEN IP LAW, LLC

(57) ABSTRACT

A refining method of a midbody of latamoxef sodium includes: dissolving 7β-amino-7α-methoxy-3-(5-tetrazolyl)thiomethyl-1-oxa-3-cephem-4-carboxylic acid in dichloromethane, and then dividing into a dichloromethane layer and a water layer; extracting the dichloromethane layer, adding a $NaHCO_3$ solution to stir, and remaining an organic layer after stratification; stirring, crystallizing and filtering the organic layer in turn, to obtain a filtrate, preparing a second powder by stirring the filtrate under conditions of a catalyst and a normal temperature; preparing a first powder by extracting the water layer, dropping the hydrochloric acid to adjust a pH value thereof, performing crystal cultivation and suction filtration after performing cooling, and then performing vacuum drying; combining the first powder and the second powder to prepare the midbody of latamoxef sodium: 7β3-amino-7α-methoxy-3-(5-tetrazolyl)thiomethyl-1-oxa-3-cephem-4-carboxylic acid, which has a yield of 95.6-96.8% and a purity of 99.2-99.5%.

9 Claims, No Drawings

REFINING METHOD OF MIDBODY OF LATAMOXEF SODIUM

BACKGROUND

1. Technical Field

The present disclosure generally relates to the field of preparing a midbody of latamoxef sodium, and especially relates to a refining method of a midbody of latamoxef sodium.

2. Description of Related Art

Latamoxef sodium, with a chemical name of (6R, 7R)-7-[2-carboxy-2-(4-hydroxyphenyl)-acetylamino]-7-methoxy-3-[(1-methyl-1H-tetrazole-5-ylthio)methyl]-8-oxo-5-oxa-1-azabicyclo[4, 2, 0]octyl-2-ene-2-formic acid disodium salt. A molecular formula is $C_{20}H_{18}N_6Na_2O_9S$, a molecular weight is 564, 45, and a structural formula is:

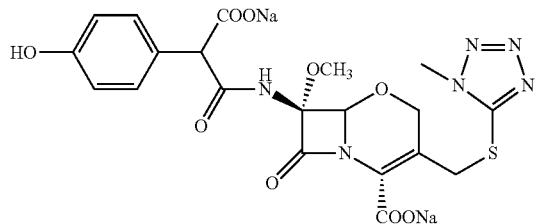

Latamoxef sodium is a semisynthetic oxycephem antibiotics developed by Yan Yeyi company of Japan in the 1980s, whose antibacterial spectrum is similar to that of cefotaxime and has a good antibacterial effect on a variety of gram-negative bacteria. In addition, there is a methoxy in a seventh position of its mother nucleus, due to steric hindrance of methoxy, it is resistant to β-lactamase that has a strong performance, and microorganisms rarely have a resistance to drugs, so it has a good market prospect. A synthesis process of latamoxef sodium is improved by He Xiaopeng et al: methoxycephem is prepared from oxycephem by methoxylation, (6R, 7R)-benzoylamino-3-(1-methyl-5-tetrazolium)-thiomethyl-7-methoxy-8-oxo-5-oxa-1-azabicyclo [4.2.0]octyl-2-ene-2-carboxylic acid diphenyl methyl ester is obtained by reacting with 1-methyl-5-mercaptotetrazolium under the catalysis of sulfonyl chloride and triethylamine, and then further optimized to finally prepare latamoxef sodium. But during the reaction, from 7β-benzamide-7α-methoxy-3-(1-methyl-1H-5-tetrazolyl) thiomethyl-1-oxa-3-cephem-4-carboxylic acid diphenyl methyl ester to 7β-amino-7α-methoxy-3-(1-methyl-1H-5-tetrazolyl)thiomethyl-1-oxa-3-cephem-4-carboxylic acid diphenyl methyl ester, and then to (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid; 7β-amino-7α-methoxy-3-(1-methyl-1H-5-tetrazolyl) thiomethyl-1-oxa-3-cephem-4-carboxylic acid diphenyl methyl ester, 7β-benzamide-7α-methoxy-3-(1-methyl-1H-5-tetrazolyl) thiomethyl-1-oxa-3-cephem-4-carboxylic acid diphenyl methyl ester, diphenyl methanol and benzoic acid are inevitably mixed into (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid, therefore, the present disclosure is provided for refining the midbody of latamoxef sodium: (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid.

Wherein a structural formula of 7β-benzamide-7α-methoxy-3-(1-methyl-1H-5-tetrazolyl)thiomethyl-1-oxa-3-cephem-4-carboxylic acid diphenyl methyl ester is:

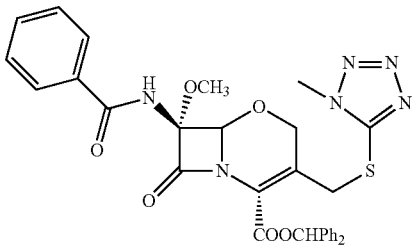

A structural formula of 7β-amino-7α-methoxy-3-(1-methyl-1H-5-tetrazolyl) thiomethyl-1-oxa-3-cephem-4-carboxylic acid diphenyl methyl ester is:

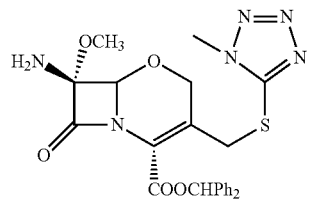

A structural formula of (6R,7R)-7-Amino-7-methoxy-3-[(1-methyl-1H-tetrazol-5-ylthio)methyl]-8-oxo-5-oxa-1-azabicyclo[4.2.0]oct-2-ene-2-carboxylic acid is:

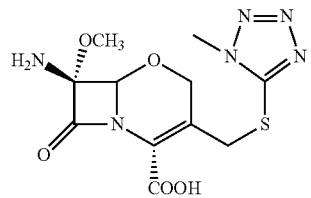

SUMMARY

The technical problems to be solved: in view of the shortcomings of the related art, the present disclosure provides a refining method of a midbody (that is (6R,7R)-7-amino-7-methoxy-3-[(I-methyl-1H-tetrazol-5-ylthio) methyl]-8-oxo-5-oxa-1-azabicyclo[4.2.0]oct-2-ene-2-carboxylic acid) of latamoxef sodium which can solve problems of a high impurity content and high costs of removing subsequent impurity. The technical scheme of the present disclosure can be implemented by the following way:

A refining method of a midbody of latamoxef sodium, with the midbody of latamoxef sodium being (6R,7R)-7-amino-7-methoxy-3-[(1-methyl-1H-tetrazol-5-ylthio) methyl]-8-oxo-5-oxa-1-azabicyclo[4.2.0]oct-2-ene-2-carboxylic acid, includes the following steps:

(1) dissolving (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid in dichloromethane and washing with an acid solution, to divide into a dichloromethane layer and a water layer;

the dichloromethane layer including 7β-benzamide-7α-methoxy-3-(1-methyl-1H-5-tetrazolyl)thiomethyl-1-oxa-3-cephem-4-carboxylic acid, diphenyl methanol and benzoic acid, and the water layer including (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid;

washing with the acid solution has two functions: one is to separate 7β-benzamide-7α-methoxy-3-(1-methyl-1H-5-tetrazolyl)thiomethyl-1-oxa-3-cephem-4-carboxylic acid from (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid; the other is to hydrolyze residual 7β-benzamide-7α-methoxy-3-(1-methyl-1H-5-tetrazolyl)thiomethyl-1-oxa-3-cephem-4-carboxylic acid diphenyl methyl ester to be (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid;

(2) extracting the dichloromethane layer, adding a NaHCO$_3$ solution to stir, to divide into an organic layer and the water layer, converting benzoic acid into sodium benzoate to enter the water layer; removing the water layer by liquid separation, to leave the organic layer;

(3) stirring, crystallizing and filtering the organic layer in the step (2) in turn, to obtain a filtrate, so as to remove diphenyl methanol crystal;

(4) extracting the water layer in the step (1) and adding hydrochloric acid, adjusting a pH value of 4-5 by using sodium hydroxide, performing crystal cultivation and suction filtration after performing cooling, and then performing vacuum drying under a temperature of 40-45° C., to prepare a first powder;

(5) stirring the filtrate in the step (3) under conditions of a catalyst and a normal temperature, washing with a NaCl solution and drying with anhydrous sodium sulfate, to prepare a second powder;

(6) combining the first powder and the second powder to prepare the midbody of latamoxef sodium: (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid; and wherein the catalyst includes any two of Ph$_2$SiH$_2$, RhH(CO)(PPH$_3$)$_3$ and RhH(PPH$_3$)$_4$ that are mixed in any proportion thereof, and a weight ratio of the catalyst to the filtrate is 0.01-0.03:1. The catalyst can be configured to reduce (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid, without affecting epoxy, ester and carboxyl groups in the molecule thereof.

Wherein the acid solution in the step (1) is a hydrochloric acid solution.

Wherein a mass concentration of the acid solution is 10-15%.

Wherein a mass concentration of the NaHCO$_3$ solution in the step (2) is 10-15%, and a stirring time is 0.5-1 h.

Wherein a stirring time of the organic layer in the step (3) is 1-2 h, and a temperature of performing crystal cultivation is 20-25° C.

Wherein a mass concentration of the hydrochloric acid in the step (4) is 3-5%, a crystallization time is 0.5-1 h, reducing the temperature to be 2-5° C., and then performing suction filtration.

Wherein a mass concentration of the NaCl solution in the step (5) is 25-30%.

Wherein the normal temperature in the step (5) is 20-30° C.

Wherein a stirring time in the step (5) is 1-2 h.

The present disclosure provides the advantages as below, compared with the related art:

(1) the present disclosure provides the midbody of (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid; that is washed with the acid solution, so that the yield is 95.66-96.82%, and the purity is 99.21-99.54%.

(2) Four compound impurities of 7β-amino-7α-methoxy-3-(1-methyl-1H-5-tetrazolyl) thiomethyl-1-oxa-3-cephem-4-carboxylic acid diphenyl methyl ester, 7β-benzamide-7α-methoxy-3-(1-methyl-1H-5-tetrazolyl)thiomethyl-1-oxa-3-cephem-4-carboxylic acid diphenyl methyl ester, diphenyl methanol and benzoic acid that are mixed into (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid, are fully removed from (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid, so that the yield and the purity are improved and the impurity content is greatly reduced.

(3) The refining method of the midbody of latamoxef sodium of the present disclosure can extract the midbody of (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid in a solid form, which can reduce a subsequent impurity removal process, ensure the quality of the midbody, and is easy for industrial production.

DETAILED DESCRIPTION

In order to more clearly understand the technical solution hereinafter in embodiments of the present disclosure, reference will now be made in detail to embodiments to further explain the present disclosure. Obviously, the implementation embodiment in the description is a part of the present disclosure implementation examples, rather than the implementation of all embodiments, examples. According to the described embodiment of the present disclosure, all other embodiments obtained by one of ordinary skill in the related art on the premise of no creative work are within the protection scope of the present disclosure.

A First Embodiment

A refining method of a midbody of latamoxef sodium is provided. The midbody is (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid, the refining method includes the following steps:

(1) dissolving (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid in dichloromethane and washing with an acid solution, to divide into a dichloromethane layer and a water layer;

(2) extracting the dichloromethane layer, adding a NaHCO$_3$ solution to stir, to divide into an organic layer and the water layer, converting benzoic acid into sodium benzoate to enter the water layer; removing the water layer by liquid separation, to leave the organic layer;

(3) stirring, crystallizing and filtering the organic layer in the step (2) in turn, to obtain a filtrate, so as to remove diphenyl methanol crystal;

(4) extracting the water layer in the step (1) and adding hydrochloric acid, adjusting a pH value thereof, performing crystal cultivation and suction filtration after performing cooling, and then performing vacuum drying at a temperature of 40° C., to prepare a first powder;

(5) stirring the filtrate in the step (3) for 1 h under conditions of a catalyst and a normal temperature of 20° C., washing with a NaCl solution and drying with anhydrous sodium sulfate, to prepare a second powder;

(6) combining the first powder and the second powder to prepare the midbody of latamoxef sodium: (6R,7R)-7-amino-7-methoxy-3-[(1-methyl-1H-tetrazol-5-ylthio) methyl]-8-oxo-5-oxa-1-azabicyclo[4.2.0]oct-2-ene-2-carboxylic acid.

The acid solution in the step (1) is a hydrochloric acid solution, and a mass concentration of the acid solution is 10%.

A mass concentration of the $NaHCO_3$ solution in the step (2) is 5%, and a stirring time is 0.5 h.

A stirring time of the organic layer in the step (3) is 1 h, and a temperature of performing crystal cultivation is 20° C.

A mass concentration of the hydrochloric acid in the step (4) is 3%, the pH is adjusted to be 4, a crystallization time is 0.5 h, reducing the temperature to be 2° C., and then performing suction filtration.

A mass concentration of the NaCl solution in the step (5) is 25%, the catalyst includes $Ph_2SiH_2$ and $RhH(CO)(PPH_3)_3$ by being mixed in a proportion of 1:1, and a weight ratio of the catalyst to the filtrate is 0.01:1.

A Second Embodiment

A refining method of a midbody of latamoxef sodium is provided. The midbody is (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid, the refining method includes the following steps:

(1) dissolving (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid in dichloromethane and washing with an acid solution, to divide into a dichloromethane layer and a water layer;

(2) extracting the dichloromethane layer, adding a $NaHCO_3$ solution to stir, to divide into an organic layer and the water layer, converting benzoic acid into sodium benzoate to enter the water layer; removing the water layer by liquid separation, to leave the organic layer;

(3) stirring, crystallizing and filtering the organic layer in the step (2) in turn, to obtain a filtrate, so as to remove diphenyl methanol crystal;

(4) extracting the water layer in the step (1) and adding hydrochloric acid, adjusting a pH value thereof, performing crystal cultivation and suction filtration after performing cooling, and then performing vacuum drying at a temperature of 45° C., to prepare a first powder;

(5) stirring the filtrate in the step (3) for 2 h under conditions of a catalyst and a normal temperature of 30° C., washing with a NaCl solution and drying with anhydrous sodium sulfate, to prepare a second powder;

(6) combining the first powder and the second powder to prepare the midbody of latamoxef sodium: (6R,7R)-7-amino-7-methoxy-3-[(1-methyl-1H-tetrazol-5-ylthio) methyl]-8-oxo-5-oxa-1-azabicyclo[4.2.0]oct-2-ene-2-carboxylic acid.

The acid solution in the step (1) is a hydrochloric acid solution, and a mass concentration of the acid solution is 15%.

A mass concentration of the $NaHCO_3$ solution in the step (2) is 10%, and a stirring time is 1 h.

A stirring time of the organic layer in the step (3) is 2 h, and a temperature of performing crystal cultivation is 25° C.

A mass concentration of the hydrochloric acid in the step (4) is 5%, the pH is adjusted to be 5, a crystallization time is 1 h, reducing the temperature to be 5° C., and then performing suction filtration.

A mass concentration of the NaCl solution in the step (5) is 30%, the catalyst includes $RhH(CO)(PPH_3)_3$ and $RhH(PPH_3)_4$ by being mixed in a proportion of 1:2, and a weight ratio of the catalyst to the filtrate is 0.02:1.

A Third Embodiment

A refining method of a midbody of latamoxef sodium is provided. The midbody is (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid, the refining method includes the following steps:

(1) dissolving (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid in dichloromethane and washing with an acid solution, to divide into a dichloromethane layer and a water layer;

(2) extracting the dichloromethane layer, adding a $NaHCO_3$ solution to stir, to divide into an organic layer and the water layer, converting benzoic acid into sodium benzoate to enter the water layer; removing the water layer by liquid separation, to leave the organic layer;

(3) stirring, crystallizing and filtering the organic layer in the step (2) in turn, to obtain a filtrate, so as to remove diphenyl methanol crystal;

(4) extracting the water layer in the step (1) and adding hydrochloric acid, adjusting a pH value thereof, performing crystal cultivation and suction filtration after performing cooling, and then performing vacuum drying at a temperature of 42° C., to prepare a first powder;

(5) stirring the filtrate in the step (3) for 1.5 h under conditions of a catalyst and a normal temperature of 25° C., washing with a NaCl solution and drying with anhydrous sodium sulfate, to prepare a second powder;

(6) combining the first powder and the second powder to prepare the midbody of latamoxef sodium: (6R,7R)-7-amino-7-methoxy-3-[(1-methyl-1H-tetrazol-5-ylthio) methyl]-8-oxo-5-oxa-1-azabicyclo[4.2.0]oct-2-ene-2-carboxylic acid.

The acid solution in the step (1) is a hydrochloric acid solution, and a mass concentration of the acid solution is 12%.

A mass concentration of the $NaHCO_3$ solution in the step (2) is 7%, and a stirring time is 0.8 h.

A stirring time of the organic layer in the step (3) is 1.5 h, and a temperature of performing crystal cultivation is 25° C.

A mass concentration of the hydrochloric acid in the step (4) is 4%, the pH is adjusted to be 4, a crystallization time is 0.5 h, reducing the temperature to be 3° C., and then performing suction filtration.

A mass concentration of the NaCl solution in the step (5) is 27%, the catalyst includes $Ph_2SiH_2$ and $RhH(PPH_3)_4$ by being mixed in a proportion of 3:1, and a weight ratio of the catalyst to the filtrate is 0.03:1.

A First Comparative Example

Compared with the first embodiment, the first comparative example does not include the step (2), and others of the first comparative example are the same as that of the first embodiment.

That is, a refining method of a midbody of latamoxef sodium is provided. The midbody is 7β-amino-7α-methoxy-3-(1-methyl-1H-5-tetrazolyl) thiomethyl-1-oxa-3-cephem-4-carboxylic acid, the refining method includes the following steps:

(1) dissolving (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid in dichloromethane and washing with an acid solution, to divide into a dichloromethane layer and a water layer;

(2) stirring, crystallizing and filtering the dichloromethane layer in the step (1), to obtain a filtrate, so as to remove diphenyl methanol crystal;

(3) extracting the water layer in the step (1) and adding hydrochloric acid, adjusting a pH value thereof, performing crystal cultivation and suction filtration after performing cooling, and then performing vacuum drying at a temperature of 40° C., to prepare a first powder;

(4) stirring the filtrate in the step (2) for 1 h under conditions of a catalyst and a normal temperature of 20° C., washing with a NaCl solution and drying with anhydrous sodium sulfate, to prepare a second powder;

(5) combining the first powder and the second powder to prepare the midbody of latamoxef sodium: (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid.

The acid solution in the step (1) is a hydrochloric acid solution, and a mass concentration of the acid solution is 10%.

A stirring time of the dichloromethane layer in the step (2) is 1 h, and a temperature of performing crystal cultivation is 20° C.

A mass concentration of the hydrochloric acid in the step (3) is 3%, the pH is adjusted to be 4, a crystallization time is 0.5 h, reducing the temperature to be 2° C., and then performing suction filtration.

A mass concentration of the NaCl solution in the step (4) is 25%, the catalyst includes $Ph_2SiH_2$ and $RhH(CO)(PPH_3)_3$ by being mixed in a proportion of 1:1.

A Second Comparative Example

Compared with the first embodiment, the second comparative example does not include the step (3), and others of the second comparative example are the same as that of the first embodiment.

That is, a refining method of a midbody of latamoxef sodium is provided. The midbody is (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid, the refining method includes the following steps:

(1) dissolving (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid in dichloromethane and washing with an acid solution, to divide into a dichloromethane layer and a water layer;

(2) extracting the dichloromethane layer, adding a $NaHCO_3$ solution to stir, to divide into an organic layer and the water layer, converting benzoic acid into sodium benzoate to enter the water layer; removing the water layer by liquid separation, to leave the organic layer;

(3) extracting the water layer in the step (1) and adding hydrochloric acid, adjusting a pH value thereof, performing crystal cultivation and suction filtration after performing cooling, and then performing vacuum drying at a temperature of 40° C., to prepare a first powder;

(4) stirring the organic layer in the step (2) for 1 h under conditions of a catalyst and a normal temperature of 20° C., washing with a NaCl solution and drying with anhydrous sodium sulfate, to prepare a second powder;

(5) combining the first powder and the second powder to prepare the midbody of latamoxef sodium: (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid.

The acid solution in the step (1) is a hydrochloric acid solution, and a mass concentration of the acid solution is 10%.

A mass concentration of the $NaHCO_3$ solution in the step (2) is 5%, and a stirring time is 0.5 h.

A mass concentration of the hydrochloric acid in the step (3) is 3%, the pH is adjusted to be 4, a crystallization time is 0.5 h, reducing the temperature to be 2° C., and then performing suction filtration.

A mass concentration of the NaCl solution in the step (4) is 25%, and the catalyst includes $Ph_2SiH_2$ and $RhH(CO)(PPH_3)_3$ by being mixed in a proportion of 1:1.

A Third Comparative Example

Compared with the first embodiment, the third comparative example does not include the step (4), and others of the third comparative example are the same as that of the first embodiment.

That is, a refining method of a midbody of latamoxef sodium is provided. The midbody is (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid, the refining method includes the following steps:

(1) dissolving (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid in dichloromethane and washing with an acid solution, to divide into a dichloromethane layer and a water layer;

(2) extracting the dichloromethane layer, adding a $NaHCO_3$ solution to stir, to divide into an organic layer and the water layer, converting benzoic acid into sodium benzoate to enter the water layer; removing the water layer by liquid separation, to leave the organic layer;

(3) stirring, crystallizing and filtering the organic layer in the step (2) in turn, to obtain a filtrate, so as to remove diphenyl methanol crystal;

(4) stirring the filtrate in the step (3) for 1 h under conditions of a catalyst and a normal temperature of 20° C., washing with a NaCl solution and drying with anhydrous sodium sulfate, to prepare a second powder;

(5) combining the first powder and the second powder to prepare the midbody of latamoxef sodium: (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid.

The acid solution in the step (1) is a hydrochloric acid solution, and a mass concentration of the acid solution is 10%.

A mass concentration of the $NaHCO_3$ solution in the step (2) is 5%, and a stirring time is 0.5 h.

A stirring time of the organic layer in the step (3) is 1 h, and a temperature of performing crystal cultivation is 20° C.

A mass concentration of the NaCl solution in the step (4) is 25%, and the catalyst includes $Ph_2SiH_2$ and $RhH(CO)(PPH_3)_3$ by being mixed in a proportion of 1:1.

TABLE 1

| | First embodiment | First embodiment | First embodiment | First comparative example | Second comparative example | Third comparative example |
|---|---|---|---|---|---|---|
| Yield (%) | 96.82 | 95.66 | 96.53 | 90.21 | 88.97 | 83.46 |
| Purity (%) | 99.21 | 99.35 | 99.54 | 97.53 | 97.18 | 99.29 |
| Diphenyl methanol content (%) | 0.08 | 0.05 | 0.06 | 0.08 | 0.92 | 0.08 |
| Benzoic acid content (%) | 0.13 | 0.09 | 0.10 | 0.84 | 0.13 | 0.13 |

A calculation formula: a yield=$(m_1/m_0)*100\%$, wherein $m_1$ is a mass of the midbody of latamoxef sodium that has been refined by the refining method of the present disclosure, $m_0$ is a theory quality of the midbody that has been obtained from the improved synthetic process of latamoxef sodium by He Xiaopeng et al. {from 7β-benzamide-7α-methoxy-3-(1-methyl-1H-5-tetrazolylthiomethyl-1-oxa-3-cephem-4-carboxylic acid diphenyl methyl ester to 7β-amino-7α-methoxy-3-(1-methyl-1H-5-tetrazolyl) thiomethyl-1-oxa-3-cephem-4-carboxylic acid diphenyl methyl ester, and then to (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid, a theory quality of (6R,7R)-7-amino-7-methoxy-3-[(1-methyl-1H-tetrazol-5-ylthio)methyl]-8-oxo-5-oxa-1-azabicyclo[4.2.0]oct-2-ene-2-carboxylic acid}; an HPLC method is used to determine the purity of the midbody of latamoxef sodium and the contents of diphenylmethanol and benzoic acid.

It can be seen from table 1 that the yield of the midbody of latamoxef sodium in each of the first to third embodiments is 95.66-96.82%, while the yield of the midbody of latamoxef sodium in each of the first to third comparative examples is 83.46-90.21%, however, the yield of the midbody of latamoxef sodium that has been obtained from the improved synthetic process of latamoxef sodium by He Xiaopeng et al, is only 80%, which is beneficial to the step of washing with the acid solution in the step (1), the hydrolysis of residual 7β-amino-7α-methoxy-3-(1-methyl-1H-5-tetrazolyl) thiomethyl-1-oxa-3-cephem-4-carboxylic acid diphenyl methyl ester, and the step (4), and also beneficial to the catalyst reduction in the step (5).

In addition, the purity of the midbody of latamoxef sodium in each of the first to third embodiments is much higher than that of each of the first and second comparative examples, which indicates that the removal of benzoic acid and diphenyl methanol in the steps (2) and (3) can greatly improve the purity of the midbody of latamoxef sodium. It can be seen from the first embodiment and the first comparative example that the benzoic acid content of the first comparative example is higher than that of the first embodiment without performing impurity removal on benzoic acid; it can be seen from the first embodiment and the first comparative example that the content of diphenyl methanol in the second comparative example is higher than that of the first embodiment without performing impurity removal on diphenyl methanol.

Although the features and elements of the present disclosure are described as embodiments in particular combinations, each feature or element can be used alone or in other various combinations within the principles of the present disclosure to the full extent indicated by the broad general meaning of the terms in which the appended claims are expressed.

What is claimed is:

1. A refining method of a midbody of latamoxef sodium with the midbody of (6R,7R)-7-Amino-7-methoxy-3-[(1-methyl-1H-tetrazol-5-ylthio)methyl]-8-oxo-5-oxa-1-aza bicyclo[4.2.0]oct-2-ene-2-carboxylic acid, the refining method comprising the following steps:
  (1) dissolving (6R,7R)-7-Amino-7-methoxy-3-[(1-methyl-1H-tetrazol-5-ylthio)methyl]-8-oxo-5-oxa-1-azabicyclo[4.2.0]oct-2-ene-2-carboxylic acid in dichloromethane and washing with an acid solution, to divide into a dichloromethane layer and a water layer;
  (2) extracting the dichloromethane layer, adding a NaHCO₃ solution to stir, to divide into an organic layer and the water layer, removing the water layer by liquid separation, to leave the organic layer;
  (3) stirring, crystallizing and filtering the organic layer in the step (2) in turn, to obtain a filtrate;
  (4) extracting the water layer in the step (1) and adding hydrochloric acid, adjusting a pH value of 4-5 by using sodium hydroxide, performing crystal cultivation and suction filtration after performing cooling, and then performing vacuum drying under a temperature of 40-45° C., to prepare a first powder;
  (5) stirring the filtrate in the step (3) under conditions of a catalyst and a normal temperature, washing with a NaCl solution and drying with anhydrous sodium sulfate, to prepare a second powder;
  (6) combining the first powder and the second powder to prepare the midbody of latamoxef sodium: (6R,7R)-7-Amino-7-methoxy-3-[(1-methyl-1H-tetrazol-5-ylthio)methyl]-8-oxo-5-oxa-1-azabicyclo[4.2.0]oct-2-ene-2-carboxylic acid; and wherein
  the catalyst comprises any two of $Ph_2SiH_2$, $RhH(CO)(PPH_3)_3$ and $RhH(PPH_3)_4$ that are mixed in any proportion thereof, and a weight ratio of the catalyst to the filtrate is 0.01-0.03:1.

2. The refining method as claimed in claim 1, wherein the acid solution in the step (1) is a hydrochloric acid solution.

3. The refining method as claimed in claim 1, wherein a mass concentration of the acid solution is 10-15%.

4. The refining method as claimed in claim 1, wherein a mass concentration of the NaHCO₃ solution in the step (2) is 10-15%, and a stirring time is 0.5-1 h.

5. The refining method as claimed in claim 1, wherein a stirring time of the organic layer in the step (3) is 1-2 h, and a temperature of performing crystal cultivation is 20-25 CC.

6. The refining method as claimed in claim 1, wherein a mass concentration of the hydrochloric acid in the step (4) is 3-5%, a crystallization time is 0.5-1 h, reducing the temperature to be 2-5° C., and then performing suction filtration.

7. The refining method as claimed in claim 1, wherein a mass concentration of the NaCl solution in the step (5) is 25-30%.

8. The refining method as claimed in claim 1, wherein the normal temperature in the step (5) is 20-30° C.

9. The refining method as claimed in claim 1, wherein a stirring time in the step (5) is 1-2 h.

* * * * *